United States Patent
Miglietta et al.

(10) Patent No.: US 8,731,964 B2
(45) Date of Patent: *May 20, 2014

(54) INTEGRATED SYSTEM FOR GENERATION AND RETENTION OF MEDICAL RECORDS

(71) Applicants: Joseph H. Miglietta, Scottsdale, AZ (US); J Barton Ripperger, Phoenix, AZ (US)

(72) Inventors: Joseph H. Miglietta, Scottsdale, AZ (US); J Barton Ripperger, Phoenix, AZ (US)

(73) Assignee: Starwriter, LLC, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/656,645

(22) Filed: Oct. 19, 2012

(65) Prior Publication Data

US 2013/0073316 A1 Mar. 21, 2013

Related U.S. Application Data

(63) Continuation of application No. 11/969,221, filed on Jan. 3, 2008, now Pat. No. 7,949,544, which is a continuation of application No. 10/871,942, filed on Jun. 18, 2004, now abandoned, which is a continuation-in-part of application No. 10/406,076, filed on Apr. 2, 2003, now abandoned.

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC ............................................................ 705/2
See application file for complete search history.

(56) References Cited

U.S. PATENT DOCUMENTS

| | | | | |
|---|---|---|---|---|
| 5,583,758 A | * | 12/1996 | McIlroy et al. | 705/2 |
| 6,208,974 B1 | * | 3/2001 | Campbell et al. | 705/3 |
| 7,949,544 B2 | * | 5/2011 | Miglietta et al. | 705/2 |

OTHER PUBLICATIONS

Saito, Medical diagnostic expert system based on PDP model, Neural Networks, 1988., IEEE International Conference on, Aug. 6, 2002.*

* cited by examiner

*Primary Examiner* — Tran Nguyen
(74) *Attorney, Agent, or Firm* — Meyer & Associates, LLC; Lee G. Meyer, Esq.

(57) ABSTRACT

A system for populating patient records by use of evidence-based relational database, which compares the medical practitioners diagnoses to predetermined responses, to produce accurate patient chart notes and the integration of stored and generated data into clinical and administrative medical record keeping and billing. Episodic encounters are developed into cases for a specific patient under the care of a practitioner. The subjective symptoms from the patient and the objective observations of the care provider concurrent with the episode are used to form a diagnosis which presents a treatment regimen from an evidence-based relational database and populates medical and administrative templates. Patient history and updated information are retained in the database. "Best practice" treatment plans are continually placed in the relational database from practice guides and experts in the field.

20 Claims, 4 Drawing Sheets

INTEGRATED SYSTEM FOR GENERATION AND RETENTION OF MEDICAL RECORDS

CROSS-REFERENCE TO RELATED APPLICATION

The present application is a Continuation Application of U.S. application Ser. No. 13/114,008 filed May 23, 2011 for "INTEGRATED SYSTEM FOR GENERATION AND RETENTION OF MEDICAL RECORDS," now pending, which is Continuation Application of U.S. application Ser. No. 11/969,221, filed Jan. 3, 2008 for "INTEGRATED SYSTEM FOR GENERATION AND RETENTION OF MEDICAL RECORDS," now U.S. Pat. No. 7,949,544, which is a Continuation Application of U.S. application Ser. No. 10/871,942 filed Jun. 18, 2004 for "INTEGRATED SYSTEM FOR GENERATION AND RETENTION OF MEDICAL RECORDS," which is a continuation-in-part application of U.S. application Ser. No. 10/406,076 filed Apr. 2, 2003 for "INTEGRATED SYSTEM AND METHOD FOR DOCUMENTING AND BILLING PATIENT MEDICAL TREATMENT AND MEDICAL OFFICE MANAGEMENT," now abandoned.

BACKGROUND OF THE INVENTION

1. Field of the Invention

The present invention relates generally to electronic generation and retention of clinical and administrative medical records; and, more particularly, to a system for populating patient records by use of evidence-based evaluation systems, which compare the medical practitioners diagnoses to predetermined objective and subjective responses, including those of experts in the field, to produce accurate patient chart notes and the integration of stored and generated data into clinical and administrative medical record keeping and billing.

2. Description of Related Art

Modern medical practices demand accurate medical records of patient history and treatment. The information maintained in a patient history and treatment record is what the physician relies on to carry out a course of treatment, and also to justify the billing for service.

Thus, medical records exist primarily for the use of health care providers to record the information related to the continuing care of each patient. These records are generally created in two ways. 1.) By historical data entry, usually subjective in nature, of a patient's past medical history and health related issues and experiences; and, 2.) by physicians and medical experts after various episodic encounters with a patient including objective observations, clinical tests, and subjective symptom gathering from the patient concurrent with the episode. Usually, as the patient experiences further and differing treatment, these records follow the patient from physician to physician. The medical record is episodically updated. From this diverse data the physician makes a diagnosis and prescribes a course or regimen of treatment. The increasing demands placed on a physician's time, however, results, too often, in patient charts and records that are improperly maintained and difficult, at best, to read.

Paper medical records have been used for many years and remain the standard way of doing things, even today. A patient's medical record is not a single file, but a multitude of records that are retained amongst many different providers, hospitals, clinics, and schools. These paper records have numerous obvious limitations and drawbacks, including a lack of legibility and inconsistency of format. Notes are often illegible, paper suffers from wear and can only be in use at one location at a time, thus making it unavailable to more than one practitioner at a time. Further, paper records require large secured (HIPPA) storage spaces as well as numerous shelves or cabinets. A staff of trained personnel must be maintained to manually file, retrieve and keep track of the records. Loss, damage, or destruction of the records can occur due to numerous mishaps such as flood, fire or even a spilled beverage. Backup of paper records is difficult, time consuming, expensive and many times not current.

Thus, many record keeping systems have become at least partially electronic to alleviate the above problems. While software programs exist to help individually manage the above areas, none of them are compatible so that one software program will manage an entire medical office. When creating patient history (personal information and medical/surgical history), for example, patients generally fill out personal and medical history information forms. This information is then entered manually into the patient file and record by office staff into the office computer system. This is a slow, time consuming, labor intensive process for the office staff/employees.

In order to bill a client, a physician has traditionally completed a superbill/patient encounter form after a patient's visit. This superbill has the diagnosis. This (ICD) code and the procedure, (CPT code) which describe the surgery or E&M code details of the encounter is required for billing the patient or insurance company. The office staff then fills out the insurance claim form (the HCFA 1500 form) manually for billing the insurance company, or the information and codes are entered manually by the office staff into a computer software system which then creates a patient file. The office staff then can enter the appropriate billing codes into the insurance claim form (HCFA 1500) which is part of the computer system. This can then either be printed out and mailed to the insurance company or sent electronically to the insurance company.

Even with the advent of automation, dictation remains the primary means of documenting patient care. The process requires a physician dictate the patient name, ID, age, and other demographic information, followed by the description of the patient complaints, the observations from the exam, the diagnosis, and description of treatments. This procedure has to be repeated for each patient encounter to assure accuracy. Because of the relationship of symptoms to diagnosis, this entails dictating repetitive medical information. Most dictation is hand transcribed into paper format for the file. Solutions have been applied to improve the dictation efficiency by using automatic speech recognition (ASR) and super macros that allow a physician to use a single phrase to describe a medical condition or treatment. ASR has to date been a disappointment due to its accuracy problems.

Many software programs exist for assisting the practitioner with billing. However, the input is still mostly manual. This process is very time consuming and labor intensive for office staff and expensive to the physician to pay for the man-hours and labor to perform the tasks required for billing. Further, little of this billing software is compatible with the software for maintaining medical records. Thus, one cannot easily import information from the medical records software to existing billing software. In addition, there are inventory and recording problems.

To add to the complexity, when a physician deems necessary, various supplies are dispensed to a patient. Some of the supplies that may be dispensed on any given office visit include, but is not limited to, splints, casts, fracture orthoses, pads bandage and dressings, orthotic devices, and braces. Currently these items etc. are dispensed/given to a patient with virtually no communication to office staff/billing employees other than recording these on a superbill, which frequently can result in missed billing for the supply and failure by the office to reorder and restock the utilized supplies.

Frequently, patients will require prescription medication from a physician for appropriate treatment of a medical problem. Currently, these are hand written on a paper prescription forms by the doctor and given to the patient to take to a pharmacy to be filled and dispensed. This method is slow and labor intensive. Also, errors can occur at the pharmacy due to inability of the pharmacist to read the handwriting of the physician resulting in medication and dosing errors for patients. Additionally, some patients lose the paper prescription and consequently never obtain necessary medication.

With the ever increasing cost of healthcare, surgeries, medications etc., it has become necessary to find means to justify cost and efficacy of medical treatments. Until now, very little can be done to identify and justify costs and efficacy of treatments. Random studies can be done in teaching hospital settings for studies on procedures. Attempts have been made to retrieve data from multiple physician offices to try to study effectiveness of various treatments and procedures. Therefore, a need exists to provide an integrated system and method for documenting and billing patient medical treatment.

Some offices have adopted Electronic Medical Records (EMR) to replace paper. These systems, although gaining acceptance in the medical profession, suffer serious limitations. Some, which are in use, involve electronic records and templates. One type involves pre-created documents that contain specific areas that are quasi-customizable for documenting specific patient information. Primary use of these templates is in administrative record keeping, such as super bills for insurance interface and the like.

Further, to facilitate use of EMR, systems have been created to aid in the process of creating these medical records. Most of the current applications, however, are designed to follow the existing paradigm used for generating a patient chart note.

These applications use a spread sheet that corresponds to a practice superbill to allow the physician to check off boxes that correspond to the treatment administered. Edit fields are available where the physician can type in information related to the specifics of the symptoms observed or to the treatment administered. While useful for gathering and storing information into a database for future retrieval, such systems are cumbersome to use and require a physician to be tied to a computer. Because this is not possible during the patient exam or treatment, the physician is still left to rely on hand written or dictated notes that are subsequently entered into the spread sheet. This has the obvious flaws of causing the possibility of inaccurate information and loss of efficiency of the physician's time, as well as, double entry.

Many medical applications software allow the practitioner to slightly modify the template information or, in some cases, create the template prior to use. In either case, population of the template involves dictation or keystroke application of information created by the practitioner. The ability to customize is often more of a hindrance to the product's adoption due to the additional burden placed on the practitioner, the emphasis having been wrongly placed on the ability to adjust the document wording as opposed to its content. While templates have the advantage of allowing for rapid chart generation, they are limited by capturing only that information generated by the practitioner to populate the template. In addition, once the template content is modified, the interactions with other aspects of EMR are modified or destroyed requiring complete alteration of the system.

Still, other systems have been designed to guide the physician through the diagnosis and treatment process. The applications queries the physician for information, makes suggestions for treatments and documents the choices and information typed in. These systems are particularly cumbersome to use, since a physician having been trained in the field of medical practice, already knows the diagnosis and treatments.

In an effort to reduce inconsistency of format the Problem Oriented Medical Record (POMR) was introduced in the 1960s by L. L. Weed. This system relies on the acronym SOAP as a standard approach to recording entries. The four parts of this acronym are expressed as follows:

Subjective—this summarizes the patient's statement of his or her concerns, history and the story of what has transpired. It includes the chief complaint or concern.

Objective—the practitioner's observations, and results of physical evaluation.

Assessment—the practitioner's opinion of diagnosis based on the subjective and objective findings.

Plan—a course of treatment or plan on what the practitioner intends to do next and instructions to the patient as to treatment and further evaluation or testing.

It is well documented within the medical profession that a specific set of symptoms, whether objective or subjective, correlates to a particular diagnosis. The problem is that the number of symptoms required to uniquely identify a particular condition and, therefore, a course of treatment, is large. Only by use of electronic data handling and information flow path analysis is a usable correlation between the two achievable.

One of the emerging techniques in patient episodic diagnosis is the use of evidence-based practice guide-lines. A problem with this technique is that professional practitioners are faced with additional data, which relates to their profession and impacts their continued ability to manage professional scenarios. Thus, these professionals, whose job it is to keep up with the latest techniques and information for problems solving, find themselves in a further information overload. This situation translates into disconcertingly low rates of compliance with widely disseminated evidence-based treatment guidelines even by very knowledgeable practitioners.

Awareness may not be the only explanation for the modest implementation rate of evidence-based "practice guidelines." The failure to use factually based scenarios and evidence-based diagnosis, revolves around the inability of the practitioner to find time to read and digest the overwhelming volume of data, which relates to their profession and impacts their continued ability to manage evidence-based professional scenarios. Thus, medical professionals find themselves in an information dilemma in an attempt to keep up with the latest techniques and information required for diagnosing based upon evidence-based practice guidelines.

Furthermore, with the passage of HIPPA regulations, EMR systems must meet very rigid security standards. Having large databases of patient related medical information, without appropriate safeguards is risky. Therefore, a requisite of any large relational database, which stores sensitive and complete medical related information associated with a particular patient, must be secure.

Finally, none of the current medical information systems make any attempt to pool the treatment data that is produced every day into a database that is easily accessible and relational to allow for outcome studies. Outcome studies have become increasingly desired and demanded by insurance companies to justify payments for patient care. Physicians would also gain empowerment to validate their practice of medicine. Currently, the National Institute of Health (NIH) is attempting to pool various databases created for specific studies into a single database. This plan still fails to address the vast amounts of data produced by private practitioners.

It would, therefore, be desirable to have an easy-to-use, accurate, secure system to facilitate the recording of patient treatment information in such a manner as to produce a chart note record, and produce billing data as well as raw treatment data useful for outcome studies. It would also be desirable that the system be minimally intrusive to a physician's manner of work thereby allowing the physician to maximize time spent with patients. For maximum efficiency, such a system should also provide means by which personnel, other than the physician, can interface with the data base to quickly schedule patients, enter demographic information, and allow patients to directly enter their medical history either through a kiosk or through an electronic interchange such as smart cards. Further, it would be advantageous to have a system, which is computer based, that would self generate much of the information now entered by the physician and cascade this generated information to populate an integrated administrative and medical record system.

SUMMARY OF THE INVENTION

The present invention provides a system and method for facilitating patient treatment, documentation, and billing among heterogeneous users. The system, which is computer based, self generates much of the information now entered by the physician and/or staff and cascades this generated information to populate an integrated administrative and medical record system.

The system employs a common repository for storage of patient demographics, medical history, treatment history, accounting and billing history, and a medical knowledge base that provides a relational data base which allows the medical practitioner and/or medical staff to quickly generate medical information based upon a diagnostic determination and cascade this generated information to populate an integrated administrative and medical record system. The system vastly simplifies the process of documenting patient care and creating detailed chart notes by simple clicks on a user interface.

The inventive system employs an automated tutorial for populating patient chart notes, and presents Treatment regimens predicated upon evidence-based "best practice." These Treatments are advantageously statistically predicated upon the strength of the evidence which is input to the database. In one aspect the system contains independent problem resolutions and opinions from recognized "experts" in the field so that a correlation between the diagnosis and the expected Treatment outcome can be rendered. Advantageously, the relational database can be continually updated as new information and/or practice guidelines become available, such that interaction of specific scenarios is predicated upon recommendations in published or otherwise available "practice guidelines" such that, as decisions are made, this feedback becomes available to the user immediately.

The system of the present invention provides a relational database for both administrative and clinical medical information. Entry of clinical data and diagnoses by users having medical knowledge; and, entry of practice management information by users having no medical background are provided wherein each user has an interface to the central database. In this manner, the patient based data and information are continually updated.

An automated method for generating medical records including chart notes, comprising the steps of: diagnosing a patient based upon objective and/or subjective symptoms and entering the diagnosis into a relational database, which correlates diagnosis to symptoms and related data to populate medical records including a patient chart note. The method includes population of both subjective and objective information.

The system employs a relational database wherein a Medical Knowledge Base, patient treatment repository, claims history repository, and practice management repository are linked to allow medical knowledged users, and non-medical knowledged users, using a uniform system protocol, to populate patient care documents.

A detailed chart note is generated from the raw treatment data and prior stored medical data based upon the physician's diagnosis. The process of assembling the chart note entails, mapping of prior patient information, diagnosis, treatments, and findings, as a grouped set with context sensitivity to a dictionary of descriptors. A language processor ensures that the descriptors are assembled in a grammatically correct manner. A report generator then fills in a report template that corresponds to the diagnosis for the patient visit. Templates are set up for every type of patient-provider transaction, such as but not limited to Initial Patient Visit, Follow up Visit, Surgical Consultation, Pre-op H & P, Surgical Report, Follow up Surgical Report, etc.

The inventive system and method are predicated upon the relationship between a set of symptoms and a specific diagnosis. Specifically, it has now been discovered that a relational database can be based upon the principle that for every diagnosis there exists a unique subset of subjective symptoms (from the set of all symptoms that describe the conditions presented for the diagnosis) such that, upon a physician rendering a specific diagnosis, the subjective symptoms verbalized by a patient are predictable and can be generated to populate the EMR. Likewise, a unique subset of objective observations (from the set of all objective observations that uniquely accompany a diagnosis) are presented such that the medical conditions observed and reported by the practitioner are clearly understood and predictable and can be generated to populate the EMR.

In one aspect, wherein multiple diagnoses are identified, the system combines the subsets in a manner that accurately reflects the predicted subjective and objective observations. The merging of subsets of subjective and objective observations is handled in one of two manners, as a simple merge or as a "rules based" merge. Where the intersection of the set of observations is the null set, simple merging applies. In this case, the observations apply to diagnoses that apply to separate and distinct body systems, e.g. integument and vascular.

Where the intersection of the set of observations is not the null set, then merging is guided by rules that operate on the set of characteristics that are defined by each observation. In practice this is handled by a bit field that defines the observation, whereon each bit corresponds to a defined characteristic. For example, two diagnoses describe an ailment related to skin diseases. One diagnosis describes an observation of skin tone, the other describes lesions. The observation related to the skin tone has a defined characteristic that is a different characteristic than lesions and therefore both observations are allowed. On the other hand, if the two diagnoses define observations of related to skin tone such that a conflict exists, e.g. one describes orange skin tone, the other pale skin tone, then resolution must be handled by either alerting the practitioner of a possible error in diagnosis, or a tertiary relational rule can be established, wherein under specific conditions one observation prevails over the other.

Where diagnoses are strongly coupled to specific anatomy, the identification of an anatomical location, allows definition of subset of diagnoses (from the set of all known diagnoses) to further narrow the possible diagnosis consistent with the anatomically specific subjective symptoms and objective observations. This allows the user with a much more specific list than the complete list of diagnoses for making the correct diagnosis. Advantageously, the system provides a rapid means by which the specific location of the pain can be documented and the affected anatomic tissue identified.

BRIEF DESCRIPTION OF THE DRAWINGS

The following drawings form part of the present specification and are included to further demonstrate certain embodiments. These embodiments may be better understood by reference to one or more of these drawings in combination with the detailed description of specific embodiments presented herein.

SYSTEM NOMENCLATURE

Figure 1:
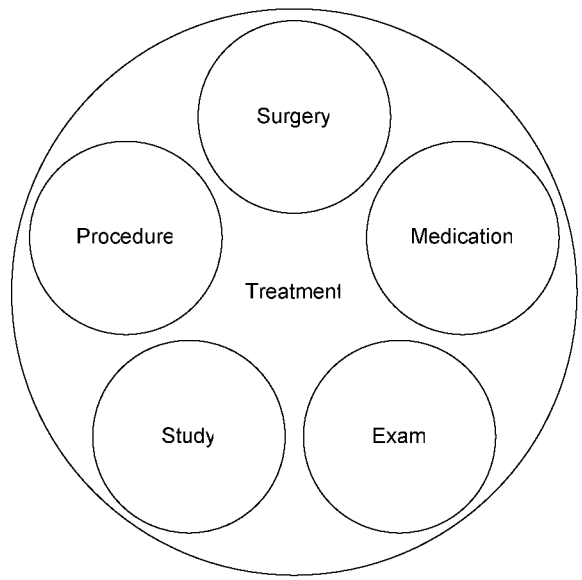
FIG. 1 is a relational diagram showing the treatment options in accordance with the system of the instant invention.

For the purposes of the present invention, the following terms shall have the following meanings:

Case: A series of patient episodes (such as appointments) which relate to an initial presenting condition for which an initial (working) Diagnoses was rendered.

Database: An indexed relational data repository, partitioned for each practice area, and distributed amongst various Servers.

Diagnosis: The medical term given to describe a specific disease or injury wherein the subjective description of symptoms and/or the objective evidence is clearly understood.

Diagnosis ID: The unique identifier of the diagnosis used within the database to identify a specific diagnosis wherein each record in the lookup table is indexed by a unique key.

Electronic Medical Records (EMR): The electronic storage of medical information including diagnosis and treatments for a patient episode in a manner such that the records can be retrieved at any time. For this system the record includes a compiled textual chart note, any associate reports, imported images, and treatment data including studies.

Episode: Any transaction between patient and practitioner defined by the location of the episode (wherein location as defined by EDI standard), the nature of the transaction (initial consultation, initial treatment, follow up treatment, surgery, etc), and date of service.

Fact: A raw data item specification that defines a range, units of measurement, method of input.

Finding: A fact that is related to a specific diagnosis, diagnosis-treatment, or treatment, that defines a default value within the fact range and related Triggers to other findings. Findings are facts that are defined within the context of a specific diagnosis, diagnosis-treatment, or treatment.

Medicore: A multiple specialty set of database tables as defined by Specialtycore.

Patient Scheduling and Management: The tasks and rules associated with scheduling patients for office visits subject to the practice management rules and status for resource availability, and management of patient invoices, claims, and accounts receivables.

Phrase: A unit of text description, that may include a limited phrase or an entire paragraph and must be narrow in scope so as to relate to a specific unit of information Practice: A medical business unit that may encompass one or more Practitioners, of the same or different specialties.

Practice ID is the identifier for the practice and is the unique key to the practice record in the indexed practices lookup table. (may be coupled with a password for security)

Practice Management: The tasks associated with managing the resources of a practice, including personnel, supplies, and inventory.

Practitioner: A medical are provider who sees patients with presenting conditions. A Practitioner is identified by Practitioner ID, which is a unique key to the Practitioner record in the indexed Practitioners lookup table.

Raw Treatment Data: The set of data that fully defines all the information recorded for a patient's episode, including Diagnoses ID, Treatment IDs, Findings data, dates, and comments.

Server: An application running behind a firewall designed to service a number of simultaneous requests for service from a multitude of users.

Specialtycore: The set of database tables that define the core information related to a given medical specialty. This includes the fundamental elements or primitives as well as the complex relationships.

Study: Any specialized means of obtaining quantifiable data, for example, radiology, blood work, biopsy, tissue sample, urinalysis, ekg, sonography, or the like.

Treatment: Any subsequent protocol performed on or by the patient, including procedures, surgery, medication, exam, Study or the like.

Treatment ID: The unique identifier of the treatment that points to the treatment record within the index treatments lookup table within the database.

Trigger: A relational link which presents secondary information based upon the particular value of a Fact.

User ID: The unique identifier of a user within the database.

Vocab: The entire set of Macros that relate Diagnoses to Phrases, Treatments to Phrases, and Findings to Phrases Web App: An application designed to operate over the Internet within a commercial browser.

Web Client App: An application designed to run as an application on a local client machine that connects to a server via for example a VPN or the Internet.

DETAILED DESCRIPTION OF THE INVENTION

The present invention is generally a system for facilitating the gathering of patient medical Treatment data useful for generating an accurate patient chart note, producing a billing claim, and for storing the raw data in a relational database format that lends itself to producing outcome studies useful for determining the efficacy of current and new medical treatments.

The system of the instant invention populates patient records by use of evidence-based evaluation systems, which compare the medical practitioners Diagnoses to predetermined responses, including those of experts in the field, to produce accurate patient chart notes and the integration of stored and generated data into clinical and administrative medical record keeping and billing.

The system, in one aspect, provides a secure, homogeneous user friendly network for recording medical treatment, practice management, and claim transactions among diverse users some of whom have medical knowledge and some that do not using a single communications link between a user and a Server(s).

The system is fully integrated, allowing medical practitioner and staff automated interface to perform the following tasks: starting a medical record/medical history for a patient file; taking chart notes/creating medical records; billing; maintaining inventory/office supplies; and prescriptions; and outcome studies.

The medical practitioner, on the basis of selecting a diagnosis, which can be anatomically directed, can generate an expected and/or predicted set of subjective symptoms verbalized by a patient as well as a set of expected medical practitioner based observations from stored medical analysis retained in a relational data base. Once accepted by the medical practitioner, this informational data is then used to autopopulate medical records. By identifying the location and diagnosis of the complaint the chart notes and reports cascading from there can be populated with a minimal of additional input.

It will be realized that the "relational aspect" of the instant invention is predicated on information flow generated around a diagnoses. The present system operates on the discovered fact that for every diagnosis there exist a unique subset of symptoms, from the set of all symptoms that describes the condition that must be present for the condition to be identified. The present system also operates on a similar assumption that for every diagnosed condition, there exists a unique subset of objective observations, from the set of all objective observations, that describes the objective observations that must be present to identify the condition Since a Diagnosis is based upon the presenting of observed conditions supported by the verbalization of various symptoms, when multiple symptoms or conditions are present, it may be possible that some symptoms overlap, or it may be possible that additional symptoms may appear as secondary or even tertiary effects. It is the latter case that presents the most difficulty in handling, as the symptom is a result of an interaction of the ailments and is not a symptom that uniquely supports the Diagnosis.

As set forth above, the present invention handles this scenario in two ways. First, the set of secondary or tertiary effects is lumped into a set of common symptoms, which can be added to the standard set of symptoms extracted for each diagnosis when more than one diagnosis is presented to the system. Second, an alarm warns the medical practitioner that two or more non-reconcilable presented symptoms are present and the possibility of the presence of additional non-verbalized symptoms. For commonly grouped conditions these symptoms are well understood and can be handled automatically. For all other cases the physician is warned and presented with the list of common interaction symptoms. In these cases further investigation is indicated before accepting the data presented by the system.

Object Model—Facts and Findings

To support the detailing of information that is specific for the particular patient, items such as temperature, size of tumor, angle of fracture, lab results, etc, the system defines a data relationship (a Fact) that defines the parameters for the information to be collected. Parameters define the units of measurement, range of value, a label for identification of the data, a default value and preferred means of inputting the information through the user interface. Not all parameters are necessarily applicable for each Fact. The value of a Fact may pull a Trigger that is a level limit for the Fact such as a blood pressure reading which results in presentment of additional queries and or related information.

Another relationship, a Finding, relates a Fact to a given Diagnosis, Treatment, or "diagnosis-treatment" combination, as further described below. For a given Diagnosis, a subset of Findings is defined, from the set of all Findings that includes all the Diagnosis specific Findings that must be collected to accurately record the symptoms and observations to support the Diagnosis. This relates to a specific medical specialty. Likewise, for a given Treatment, a subset of Findings is defined, from the set of all Findings that includes all the Treatment specific Findings that must be collected to document the Treatment.

An example of the above would be a Diagnosis which results in a prescribed Treatment regimen comprising medication. The Findings would include the medication name, dose, quantity, sig, etc. A Finding allows Diagnosis-specific data to be collected for a given Treatment. For example, if the Treatment is an X-ray, then the Findings will prompt for fracture information if the Diagnosis is a limb fracture, or percent lung damage if the X-ray is of the chest for a Diagnosis of lung cancer. As can be seen, a matrix is provided such that anatomy based information or disease based information is used by the system to "interpret" results.

Episodes and Cases

In a further aspect, the relational Database relates a Finding to the data that is actually input for a specific patient Episode. This Episode Finding includes all the Findings that were collected for documenting the specific patient Case. A Case relationship is defined as that which relates the actual occurrence of a specific Diagnosis for a patient. A Case includes the date the patient was diagnosed, the diagnosis, the medical practitioner, and other information. Other relationships, Case Treatments, Case Findings, Case anatomy, Case supplies define the actual treatments, findings, affected anatomy, and supplies used, respectively for each patient visit related to a specific Case in progress. An Episode journal record is then generated by the system to track the date of the Episodes in a patient Case to be used for charting the progress of a patient's Treatment.

Database Design—Medical Specialty Fundamental Tables

It will be realized by the skilled artisan that Diagnoses actuated databases are based on presenting symptoms and observations which relate to specific medical specialties. Thus, orthopedic surgeons and cardiologists have a differing diagnostic database. The data making up the core information that defines a medical specialty is referred to here as the Specialtycore. The group of Specialtycores making up each specialty comprises a Medicore data group. The data in each Specialtycore can be further grouped into a data set comprising fundamental components. Examples of some of these data components are anatomy, Diagnosis, Fact, phrase, supply, and Treatment. Database identifiers are established for each component such that it is referenced as a data grouping or entity. For example, an anatomy group defines a name and tissue type; a Diagnosis entity defines a name, billing code, and tissue type; a Fact entity defines a name, range of value, and units; a Phrase defines a tag (a unique name), descriptor, and lexical; a Supply (any medical supply such as syringes, cotton swaps, etc) defines a name and billing code; and a Treatment entity defines a name, type, and billing code. These examples define the minimum set of fields contained within a group, and it is understood that an actual implementation will contain more detail. A set of entities comprises a first grouping or group "A".

Medical Specialty Relational Tables

More complex entities are built from the base group A. A second, more complex grouping, Group "B" (Entities) relationships, represent the next level of complexity in the hierarchy. These tables define a higher order of information that establish relationships, as well as, include other additional unique information. Examples of group B tables include, but are not limited to, body view, Finding, macro, plan, region, risk, tray, view, and Vocab. It will be realized by the skilled artisan that table hierarchies can be built in the system, each with a relation to a subset of the lower tables to add functionality and capability to the system.

For example, a body view relates to a set of anatomy regions visible from a related view; a Finding relates Diagnosis, Treatment, and one or more Facts which together define a default value; a macro relates to Phrase and defines formatting rules and special circumstances which are discussed in more detail later; a Plan (the set of treatments selected by a practitioner to treat a diagnosis) relates a Treatment-set to Diagnosis, and a weighted factor based on "best practice" guidelines; a region defines a body location and relates to anatomy by defining a set of contents; a tray defines a name, relates to Treatment, and relates to supply by defining a set of contents; and a Vocab that relates Diagnosis to Phrase, Treatment to Phrase, Finding to Phrase.

Patient and Practice Tables

To record the actual data gathered during an Episode, another group of data is defined, called the Practicecore, (the set of tables that is specific to storing the case specific treatment information, patient and practitioner demographics, practice information) exists outside the Specialtycore and relates specific patient information to the Specialtycore, the most basic element of which is the case. As explained earlier, a Case includes the date when a diagnosis is made, and contains the set of records that include all Treatment information for each Episode related to the Case. In addition, a case encapsulates a diagnosis-anatomy-temporal set of transactions. An Episode encapsulates, for example, a patient office visit. A case is supported by the additional sub elements—Case anatomy, Case Findings, Case Treatments, and Case supplies.

A Case anatomy defines the specific region-anatomy, journal record identifier, and Case identifier. Flexibility is provided to allow for changes to the affected anatomy during the course of Treatment. For example, for a patient being treated for a skin condition as the affected region changes, the changes are documented with each visit. Case Findings document the specifics related to the Case that can not be assumed. Some examples of these measurements are temperature, blood pressure, white blood cell count, size of an ulcer, etc. Case Findings also allow for structuring data for use in outcome studies, where treatment is correlated to measured changes, or for demographic studies in which the occurrence of certain diseases is related to geographic region, patient gender, age, etc. Case Treatments record the treatments applied during each office visit. A Case Treatment is the record of treatment for the office visit. A Case Treatment relates a journal record identifier to a Case identifier and Treatment identifier. The set of Case Treatments for a given Eposode provides the set of codes used for producing a billing claim. An Episode journal table contains the information that links the patient table, Episode date, and appointment to the case table. A given Epesode corresponds to a single journal entry.

Root entities in the Specialtycore are defined in a hierarchal order, referred to as parent-child relationships. A child is able to inherit or override attributes of the parent in much the same manner as object oriented programming languages, such as C++. The hierarchy is particularly powerful for building and maintaining the Specialtycore.

Diagnostic Input

The system employing a database portioned wherein a Medical Knowledge Base, patient treatment repository, claims history repository, and practice management repository are linked, allowing users having medical knowledge and users having no medical background, using a uniform system protocol, to route transactions to document patient care.

A Medical Knowledge Base (MKB) comprised of ordered data sets and relational links provides the core data that is used to assemble a medical chart record. The Medical Knowledge Base is partitioned into specialty specific databases, hereafter referred to as the Specialtycore, and practice specific data referred to as the Practicecore. The combined set of Specialtycores that comprise the knowledge base for each specialty makes up the Medicore. The Medicore is the master database that unifies all the medical specialties, such that overlapping knowledge between specialties is not redundantly identified. The system offers the "best practice" for Treating for each Diagnosis by relating a subset of preferred Treatments from the set of all treatments as recommended by the prominent authorities in each specialty.

The Medical Service (the application that implements the means to select a patient from an appointments list, input anatomical location, diagnosis, and treatments, and generates the patient chart note) component controls the entry and routing of requests from users having medical knowledge to the MKB, while the Practice Management component controls the entry and routing of requests from Users with no medical background to the MKB. The system employs a security protocol that prevents unauthorized users from viewing sensitive patient medical history of treatment data as specified by the HIPAA act. Patients are assigned to a primary care provider within a practice. The primary care provider controls access to the patient medical records and an assign temporary access to other providers. Other users with no medical background can be assigned additional privileges in order to complete billing tasks.

Based on the anatomic location, a constrained list of diagnoses is queried from the database. Advantageously, a user having medical knowledge selects a diagnosis from the constrained list of diagnoses related to the anatomy. A list of related or differential diagnoses is queried based on the selected diagnosis. The User having medical knowledge can select any additional diagnoses from this additional list. Where an additional diagnosis is required due to payer requirements, the additional diagnosis is also indicated with an explanation for the inclusion. If the User having medical knowledge selects any of the differential diagnosis, a modifier rule used for billing will trigger when the claim is assembled at a later stage.

Other embodiments allow the user having medical knowledge to enter the diagnosis through other means such as through hand writing recognition, voice recognition, or typing. Letter matching can be employed to display the constrained list as the user types, or through voice menu prompts. It is understood that the means of data entry can be any means.

Based on the primary diagnosis, a query is made to produce a list of treatments. A "best practice" Treatment can be indicated as a guide or teaching tool. A past treatment can be indicated if the patient has any treatment history from a prior visit. From the constrained list of treatments related to the diagnosis, a treatment is selected. As in the case for specifying the diagnosis, any means of data entry can be employed for specifying the treatments. The User having medical knowledge can also specify a planned treatment for a subsequent visit to reflect the choices discussed with the patient. Special treatments under the exam category allow the user to enter additional findings that more accurately document the patient's specific condition. Exams trigger rules in the billing component to add modifiers that change the way the office visit is billed.

A list of required findings is queried based on the chosen anatomy, diagnosis, and treatments. The findings are additional facts that help to detail information specific to the patient and its diagnosis and treatment. Facts also include triggers. Triggers are relational rules for preset limits on the data range. Fact Triggers based on the finding data prompt the user for still additional findings, while Macro Triggers based on the data cause the report description to vary. For example, a high temperature reading may alert the user to take a blood pressure reading, and in the report the patient would be indicated as having fever as opposed to a normal temperature. Findings are entered through a variety of user interface means such as, check list box, radio buttons, slider, drop list box, calendar, dictation box, hand writing control and more.

Turning to FIG. 1, there is shown a relational diagram between the indicated treatments in accordance with a diagnosis protocol. A care provider examining a patient renders a Diagnosis in accordance with subjective verbalized symptoms and objective observations and/or Study data and selects a Diagnosis as previously described (not shown.) The system based on the diagnosis suggests a "best practice" Treatment schema comprised of surgery, medication, further examination, further Study, or an additional procedure. The physician then has the option, based upon the "best case" treatments, which are ranked according to evidence based outcomes. The physician then can choose the Treatment indicated which most closely is aligned with the diagnosis.

FIG. 1, thus, shows the classification of Treatment groups which share a common characteristic to allow for definition of default behavior which is common to the class. For example, all prescription Medications require data for dose, refills, quantity, and SIG; all surgery automatically generates a task to remind office personnel to verify patient insurance before the scheduled surgery; Studies include Labwork, Radiology, ultrasound, etc. Exam includes anatomy system examinations, such as a biomechanical exam, or vitals exam, and evaluations, such as a current medication use assessment, allergies assessment. Thus, each Treatment generates a generic database of related tasks which populates the records to accomplish that Treatment.

Thus, Treatment object relationships are built on a parent child basis, wherein the root parent type of Treatment defines behavior for all the Treatment classes. The Procedure module defines a baseline for all Treatments of type Procedure, etc. Parent-Child relationships can then exist to any level within each Treatment class.

Figure 2:
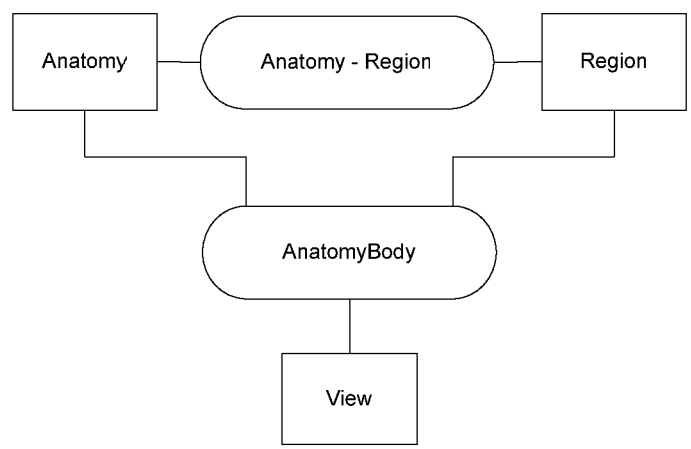
FIG. 2 is a relational diagram using the anatomy aspect in accordance with the instant invention.

FIG. 2 shows the relationship between the Specialtycore tables Anatomy, Region, and View. Anatomy defines the entire set of anatomy structure specific to a given medical specialty. View defines the entire set of perspective views of the body specific to a given medical specialty. Region defines the entire set of regions portioned from the body in every defined perspective view. The tables Anatomy-Region and Region-View are relational tables. Anatomy-Region defines the entire set of Anatomies contained in each Region, by relating Anatomy ID to Region ID. Anatomy-Region relates the entire set of regions contained in each View.

Figure 3:
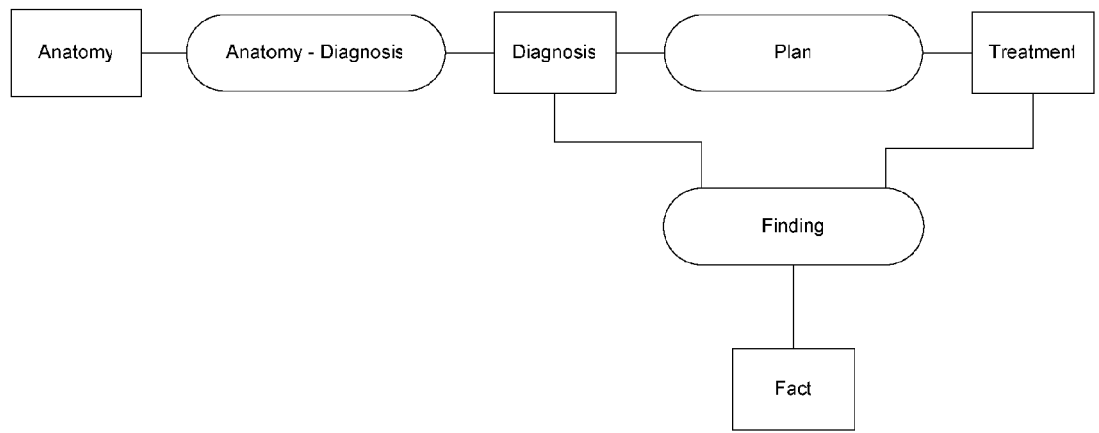
FIG. 3 is an informational flow diagram showing the relation between the diagnoses using the anatomy aspect in accordance with the instant invention.

FIG. 3 shows the relationship between the Specialtycore tables Anatomy, Diagnosis, Treatment, and Fact. Diagnosis contains the entire set of diagnoses related to the medical specialty. Treatment defines the entire set of treatments for the medical specialty, wherein each Treatment is classified into one of the Treatment groups as shown in FIG. 1. Fact defines the entire set of raw facts for the medical specialty.

The tables Anatomy-Diagnosis, Plan, and Finding are relational database look up tables. Anatomy-Diagnosis defines the entire set of Diagnoses that are possible for each Anatomy. Additionally, Diagnosis defines the specific type of anatomy issue to which each Diagnosis relates. Plan defines the regimen of treatments that are useful for treating each diagnosed condition in the specialty. In addition, those Treatments that are the preferred for each Diagnosis are flagged along with the statistical efficacy defined as a percentage of each Treatment as it relates to each Diagnosis. Findings define the set of Facts that are related to each Diagnosis, Diagnosis-Treatment pair, or Treatment.

Figure 4:
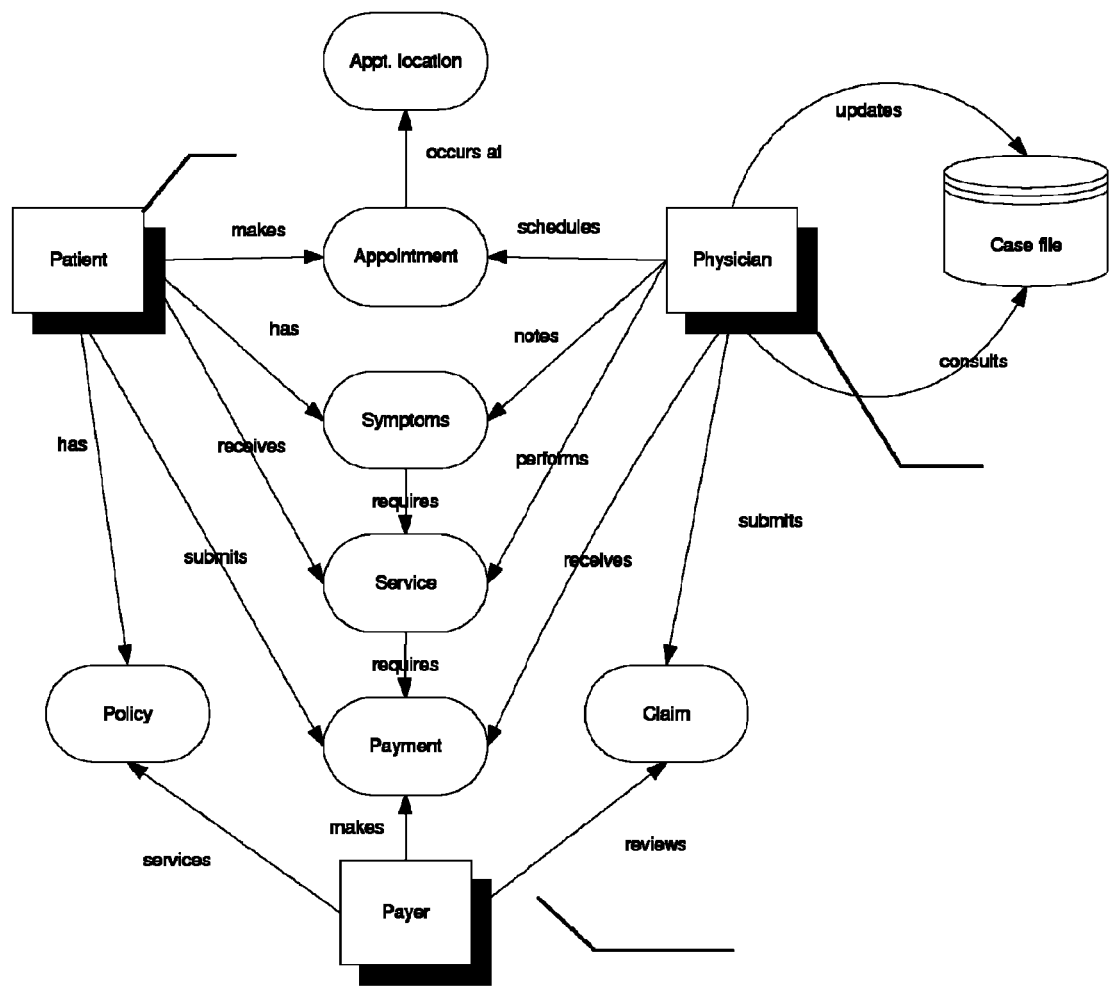
FIG. 4 is an information schema showing information flow in accordance with one aspect of the system of the instant invention.

FIG. 4 shows the entire flow path of tasks that occur in the process of patient Treatment and the relationship of Patient, Physician, and Payer. A Patient makes an appointment for a specific location, has symptoms, receives treatments, submits payment, and has an insurance policy. A Physician (or physicians office) schedules a patient for a specific location, makes note of patient's symptoms, performs treatments, updates the patient case file, consults the patient case file for medical history information, submits a claim, and receives payment. Payer services the patient policy, reviews claim information, and makes payment. This system is the framework in which the instant system operates.

Figure 5:
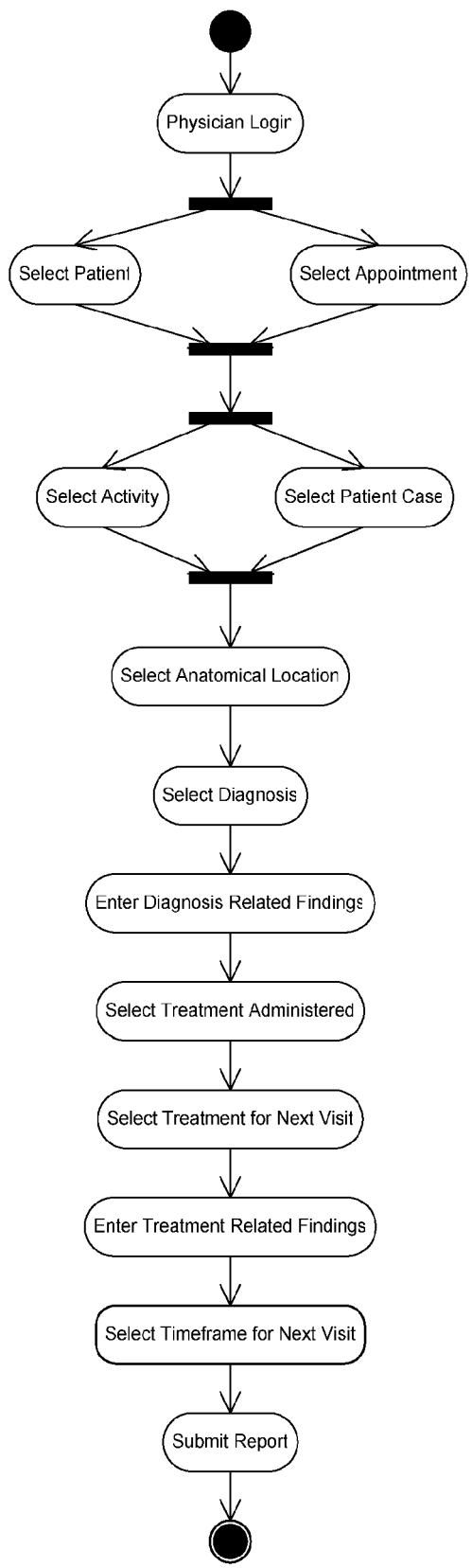
FIG. 5 is an information flow diagram from physician login to system report submission in accordance with one aspect of the instant invention.

Turning to FIG. 5, there is shown the work flow path for generating a patient chart file update in accordance with the invention. The work flow of the inventive system and method operates within the information scenario as shown in FIG. 4 above. A healthcare provider logs on the system by use of a Practitioner ID and providing a security credential. He then selects a patient either from an appointment slot or from the list of patients defined for the practice. Based upon that selection, a case is opened or retrieved depending upon the activity.

A physician then selects the anatomical location corresponding to the location of the chief complaint (subjective symptom). From a constrained list of possible Diagnoses, generated from the table Anatomy-Diagnosis (shown in FIG. 3), the healthcare provider selects the hypothesized (working) Diagnosis. Then, the healthcare provider enters any information into the set of diagnosis-related Findings, where those findings related to subjective and objective observations have default values that correspond to what should be observed and verbalized for the selected Diagnosis. The set of Treatments administered for the Episode are then checked off from the list of acceptable Treatments for the given Diagnosis. Those Treatments that are defined as the "standard of care" are selected by default by the system, but can be changed by the healthcare provider. Next, a Treatment regimen or plan is presented and again accepted or modified by the healthcare provider. Where the Treatment is case related, the system default continues previous Treatments. Next, information for the Treatment related Findings is entered. Finally, a timeframe is selected for the next Episode or, alternatively, the physician can schedule the patient directly for the next appointment.

What is claimed is:

1. A computer based, method for managing, generating and updating an individual patient's practice core database medical records to produce accurate chart notes, billing statements, and administrative records based upon a medical practitioner's input of at least one episodic medical diagnoses and at least one measurement associated with a case finding, which can be anatomically directed, of the individual patient wherein said practice core database contains an individual patient's clinical and administrative medical records, including prior treatment regimens, historical documentation, chart notes; and, billing information; and, wherein the medical practitioner's input of at least one episodic diagnoses and at least one measurement associated with a case finding generates from a relational database stored objective observations and/or subjective symptoms of a patient for updating said practice core database and populating detailed patient records and chart notes, including said case findings which deviate from the default values in said diagnosis comprising the steps of:

(a) inputting at least one of the medical practitioner's episodic diagnosis and at least one measurement associated with a case finding;

(b) generating within the relational database, based upon at least one of said medical practitioner's input episodic diagnosis, an electronic correlation between said input episodic diagnosis and at least one practice related diagnoses ID, wherein each diagnoses ID contains: i. stored general medical analysis, including an expected set of subjective symptoms predicted to be verbalized by a presenting patient; ii. a set of expected medical practitioner based observations; iii. at least one treatment ID; and, iv. at least one finding having a default value;

(c) displaying, on a display device, said stored general medical analysis, and an expected set of subjective symptoms predicted to be verbalized by a presenting patient, as well as a set of expected medical practitioner based observations on an output device by transformation of said electronic correlation; a set of correlated treatment IDs, and a set of correlated findings wherein said case findings which deviate from said default values in said diagnosis ID are substituted for at least part of said findings;

(d) accepting at least one stored general medical analysis or part thereof; and optionally accepting a set of said treatment IDs and said findings including the case findings which deviate from the default values of said findings generated by the relational database in response to said input;

(e) integrating the accepted general medical analysis, accepted treatment ID, accepted findings, including said correlated findings into the individual patient's practice core database to update said individual patient's practice core database;

(f) creating detailed patient episodic records and chart notes by activating a user interface to automatically manage and update said individual patient's clinical and administrative medical records.

2. The method of claim 1 wherein the relational database correlates said diagnosis ID to a set of treatment IDs associated with said diagnosis ID.

3. The method of claim 1 wherein said treatment ID's data contains best practices.

4. The method of claim 1 wherein said treatment IDs are evidence based.

5. The method of claim 1 wherein said measurements have a value that deviates from the finding default value and are integrated as case findings into the individual patient's practice core database to update said individual patient's episodic records and charts.

6. The method of claim 1 wherein said anatomical direction, inputted by a medical practitioner, is integrated as case anatomy into the individual patient's practice core database to update said individual patient's episodic records and chart notes.

7. The method of claim 1 wherein said medical records include a super bill.

8. The method of claim 1 wherein said relational database includes data to aid in statistical evaluation of efficacy of treatment regimens.

9. The method of claim 1 further comprising a report generator to populate a template with information from said relational database that corresponds to the medical practitioner's episodic diagnoses of the individual patient.

10. An automated system for episodically managing, generating and updating an individual patient's practice core database medical records to produce accurate chart notes, billing statements, and administrative records based upon a medical practitioner's input of at least one episodic medical diagnoses, which can be anatomically directed, of the individual patient during an episode comprising:

a. an electronic practice core database, stored on a medium, which contains an individual patient's clinical and administrative medical records, including prior treatment regimens, historical documentation, chart notes; and, billing information;

b. at least one relational database, stored on a medium, which correlates at least one of said medical practitioner's input episodic diagnosis to at least one practice related diagnoses ID, which contains stored general medical analysis, including an expected set of subjective symptoms predicted to be verbalized by a presenting patient, as well as a set of expected medical practitioner based observations; at least one treatment ID; and, at least one finding having a default value;

c. a database interface for inputting at least one of the medical practitioner's at least one episodic diagnosis and at least one measurement associated with a case finding into said relational database to generate said correlated, stored general medical analysis for the practice related to at least one diagnosis ID and a set of correlated findings wherein said case findings which deviate from said default values in said diagnosis ID are substituted for at least part of said findings;

d. a display device for displaying to said medical practitioner, said correlated stored general medical analysis, including an expected set of subjective symptoms predicted to be verbalized by a presenting patient, as well as a set of expected medical practitioner based observations; a set of correlated treatment IDs, and a set of findings wherein said case findings which deviate from said default values in said diagnosis ID are substituted for at least part of said findings;

e. a user interface for accepting at least one stored general medical analysis or part thereof generated by the relational database in response to said input, and, integrating the accepted general medical analysis into the individual patient's practice core database to update said individual patients practice core database; and, f. a report generator for reading an updated individual patient's practice core database to produce said individual patient's clinical and administrative medical records.

11. The system of claim 10 wherein the relational database correlates said diagnosis ID to a set of treatment IDs associated with said diagnosis ID.

12. The system of claim 10 wherein said treatment ID's data contain best practices.

13. The system of claim 10 wherein said treatment IDs are evidence based.

14. The system of claim 10 wherein the relational database correlates each treatment ID associated with said diagnosis ID to a set of findings associated with each treatment ID wherein each finding has a default value.

15. The system of claim 10 wherein the relational database correlates each treatment ID associated with said diagnosis ID to a set of findings associated with each treatment ID and said diagnosis ID wherein each finding has a default value.

16. The system of claim 10 wherein said medical records include a super bill.

17. The system of claim 10 wherein said relational database includes data to aid in statistical evaluation of efficacy of treatment regimens.

18. The system of claim 10 wherein said relational database comprises a medical knowledge base, a patient treatment repository, a findings repository, a claims history repository, and practice management repository and a repository of case finding containing measurements which deviate from the findings default values.

19. The system of claim 10 wherein said detailed chart note is generated from the raw treatment data and prior stored medical data based upon the physician's diagnosis by mapping prior patient information, diagnosis, treatments, and findings, as a grouped set with context sensitivity to a dictionary of descriptors.

20. The system of claim 10 further comprising a security protocol that prevents unauthorized users from viewing sensitive patient medical history of treatment data.

* * * * *